(12) United States Patent
Weber et al.

(10) Patent No.: US 10,391,091 B2
(45) Date of Patent: Aug. 27, 2019

(54) METHOD OF MANUFACTURING BUPRENORPHINE AND ANALOGUES THEREOF FROM ORIPAVINE

(71) Applicant: SIEGFRIED AG, Zofingen (CH)

(72) Inventors: Beat Theodor Weber, Gualala, CA (US); Lionel Roux, Hegenheim (FR)

(73) Assignee: Siegfried AG, Zofingen (CH)

(*) Notice: Subject to any disclaimer, the term of this patent is extended or adjusted under 35 U.S.C. 154(b) by 0 days.

(21) Appl. No.: 15/527,540

(22) PCT Filed: Oct. 13, 2015

(86) PCT No.: PCT/EP2015/073646
§ 371 (c)(1),
(2) Date: May 17, 2017

(87) PCT Pub. No.: WO2016/078833
PCT Pub. Date: May 26, 2016

(65) Prior Publication Data
US 2017/0319574 A1    Nov. 9, 2017

(30) Foreign Application Priority Data
Nov. 19, 2014  (EP) .................... 14193857

(51) Int. Cl.
C07D 489/12    (2006.01)
A61K 31/485    (2006.01)

(52) U.S. Cl.
CPC .......... *A61K 31/485* (2013.01); *C07D 489/12* (2013.01)

(58) Field of Classification Search
CPC ........................ C07D 489/12; C07D 489/02
USPC ..................................... 546/39, 44
See application file for complete search history.

(56) References Cited

U.S. PATENT DOCUMENTS 8,357,802 B2 * 1/2013 Huang ................. C07D 489/08
546/44
2009/0156817 A1    6/2009 Wang et al.

FOREIGN PATENT DOCUMENTS

| CZ | 279821 B6 | 5/1993 |
|---|---|---|
| EP | 1 439 179 | 7/2004 |
| GB | 1064539 | 4/1967 |
| WO | 2007081506 | 7/2007 |
| WO | 2008048957 A1 | 4/2008 |
| WO | 2009122436 | 10/2009 |
| WO | 2010067101 | 6/2010 |
| WO | 2010121369 | 10/2010 |

OTHER PUBLICATIONS

Caroll, F. et al., "Carbon-13 Nuclear Magnetic Resonance Spectra of Morphine Alkaloids", The Journal of Organic Chemistry (1976), vol. 41, No. 6, pp. 996-1001.
Werner, L. et al., "Synthesis of Buprenorphine from Oripavane via N-Demethylation of Oripavine Quaternary Salts", The Journal of Organic Chemistry (2011), vol. 76, No. 11, pp. 4628-4634.
International Search Report for PCT/EP2015/073646 dated Nov. 19, 2015.
Bentley & Hardy J. American Chemical Society (1967) 89(13): 3273-3280.
Bentley et al. J. American Chemical Society (1967) 89(13): 3267-3273.
Andre et al. (1992) Synthetic Communications 22(16): 2313-2327.
DeGraw et al. (1978) Journal of Medicinal Chemistry 21(5): 415-422.
Burwell Jr. (1954) Chemical Reviews, 54: 615-685.
Contribution of Observation by Third Party for EP 15778960.3 dated May 23, 2018.

* cited by examiner

*Primary Examiner* — Charanjit Aulakh
(74) *Attorney, Agent, or Firm* — Hunton Andrews Kurth LLP

(57) ABSTRACT

The invention relates to an improved method of preparing buprenorphine, a salt thereof, analogs of buprenorphine and their salts. In particular, the invention relates to a method of preparing buprenorphine and related products and salts in economic and ecologic ways having increased yields.

12 Claims, No Drawings

METHOD OF MANUFACTURING BUPRENORPHINE AND ANALOGUES THEREOF FROM ORIPAVINE

CROSS-REFERENCE TO RELATED APPLICATIONS

This patent application is a national stage application of International Patent Application No. PCT/EP2015/073646, filed Oct. 13, 2015, which claims priority to European Patent Application No. 14193857.1, filed Nov. 19, 2014, the disclosures of each of which are herein incorporated by reference.

FIELD OF THE INVENTION

The present invention relates to an improved method of preparing buprenorphine, analogues of buprenorphine or salts thereof, as well as a product produced by the method of the invention and the use of the product in a pharmaceutical formulation as well as the pharmaceutical formulation. In particular, the invention relates to a novel efficient method having economic and ecologic advantages.

STATE OF THE ART

Buprenorphine (cyclopropylmethyl-7-[(S)-3,3-dimethyl-2-hydroxybutan-2-yl]6-methoxy-4,5-epoxy-6,14-ethano-morphinan-3-ol), generally administered in the form of its hydrochloride salt, is a potent semi-synthetic opiate analgesic, for the relief of moderate, chronic and acute pain, as well as in the therapy of opioid addiction. Since its approval it has been marketed as injectable solution, various types of tablets or patches. Buprenorphine can be administered as sole active ingredient or in combination with other substances such as naloxone, for example.

18,19-dihydroetorphine, an analogue of buprenorphine, can be used as strong analgesic. Its clinical properties indicate administration as sublingual tablet or transdermal patches. Main application fields are the treatment of very intense pains and to treat addicts. Even though the potency of 18,19-dihydroetorphine is several thousand times higher than that of morphine, the observed side effects are mild.

Buprenorphine and 18,19-dihydroetorphine can be shown by the following formula (II) wherein R' is methylcyclopropyl, R" is tert-butyl and R'" is H in case of buprenorphine, and wherein R' is methyl, R" is n-propyl and R'" is H in case of 18,19-dihydroetorphine.

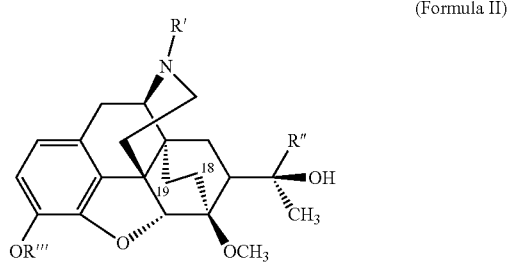

(Formula II)

It is desirable to develop economic and ecologic methods to manufacture such substances and their pharmaceutically acceptable salts.

Several methods for synthesizing buprenorphine from compounds isolated from the opium poppy or compounds derived therefrom are known. The most conventional ones use thebaine as starting material, which is shown in Formula I below wherein R is a methyl group and R'" is methyl. WO 2003/024972 and WO 2004/020220 (EP 1 439 179) disclose a classical route of synthesis from thebaine to buprenorphine and to analogues thereof. The synthetic route is a series of chemical reaction steps, including (i) adding methyl vinyl ketone to thebaine, (ii) hydrogenation of the 18,19 etheno group, (iii) addition of the tertiary butyl group by a Grignard reaction, (iv) 17-N-demethylation and introducing of a cyano group (2 steps), (v) 3-O-demethylation, (vi) hydrolysis of 17-N-cyano group, and (vii) addition of a cyclopropyl methyl group.

The number of steps, the low yield in some critical steps and the restriction to thebaine as starting material are serious drawbacks of this method.

WO 2007/081506 (EP 1 981 891) describes a process for preparing buprenorphine from oripavine, which is shown in formula I below wherein R is a methyl group and R'" is H, and which also shows the numbering of carbon atoms in the structure of oripavine and analogues as well as products derived therefrom. The process comprises a series of 8 chemical reactions, following along the conventional route as described when using thebaine as starting substance. Drawback of this route is the need to protect the hydroxyl group in position 3 when using oripavine as starting material. Reported yield over all steps is calculated to less than 11.5%.

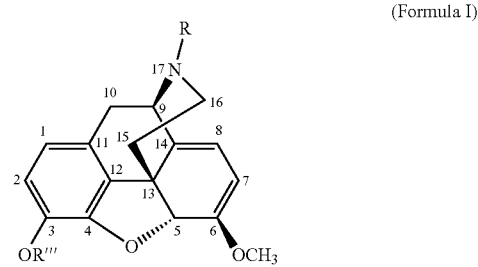

(Formula I)

Werner et al. (Werner, L.; Machara, A.; Adams, D. R.; Cox, D. P.; Hudlicky, T.; J. Org. Chem. 2011, 76, 4628-4634) describe a synthesis starting from oripavine. However, only a low yield can be obtained or a need for further reaction steps arises for obtaining high yields of buprenorphine. Also particular steps have been disclosed. WO 2010/039210 (EP 2 342 206) for example describes the hydrogenation of the 18,19 etheno group.

A problem of the actual known methods of preparing buprenorphine is that the preparation still requires many steps, a long process time and includes rather complicate and also critical steps. Further, each step reduces yield, and therefore has an impact on economic and ecologic factors. There is a need for new routes for the synthesis of buprenorphine and analogues thereof.

In addition, there is further a need to optimize the process for synthesizing buprenorphine and analogues thereof from an economic and ecologic point of view.

Thus, an object of the present invention is to provide an improved, more efficient, method of obtaining buprenorphine or a salt thereof, an analogue of buprenorphine or salts thereof.

SUMMARY OF THE INVENTION

The current invention offers a novel method for manufacturing buprenorphine, 18,19-dihydroetorphine and other analogues thereof, as well as acid addition salts. An economic and ecologic way is presented to manufacture the desired substances using a novel sequence of reaction steps delivering a satisfying yield and without the known and explained drawbacks of actual procedures.

The inventors found that such substances or salts thereof can easily be produced by choosing a novel series of reactions and thus avoiding some of the conventional reaction steps, mainly the protection of a side chain. In addition, an elegant way of substituting the N-methyl group by any alkyl group has been found. Further, an increased yield can be obtained with the novel method.

Additionally, it was found out that it is effective to carry out the steps with low yield earlier in a reaction sequence in order to reduce production cost and ecological impact, as the amount of e.g. solvents and energy can be reduced. The inventors found out that it is possible to carry out the production of buprenorphine and analogues thereof with an increasing yield in the steps by carrying out first the conversion of the acetyl group in position 7 into a tertiary alkyl alcohol and then reducing the etheno group in position 18,19 of the buprenorphine structure, contrary to the route commonly applied in the state of the art. Furthermore, the amount of an expensive catalyst used can be reduced when carrying out the reducing step (iv-a) after the step of converting the acetyl group in position 7 (iii-a), i.e. in a later step, compared to carrying out the reducing step (iii-b) before the conversion step of the acetyl group in position 7 (iv-b), thus also reducing inevitable losses of such catalyst as well as avoiding further waste material.

In one aspect, the present invention relates to a method of preparing a compound of Formula II, or a salt thereof, from a compound of formula I, wherein in Formula II R' represents a linear, branched and/or cyclic alkyl group having 1 to 10 carbon atoms, R" represents a linear, branched and/or cyclic alkyl group having 1 to 10 carbon atoms, and R''' represents H or a linear, branched and/or cyclic alkyl group having one to 6 carbon atoms, comprising:

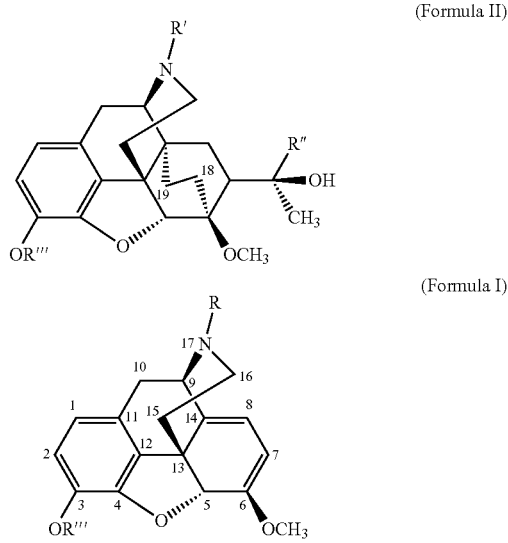

(i) optionally replacing the group R in the compound of Formula I, wherein R is H or methyl, by a group R' being a linear, branched and/or cyclic alkyl group having 1 to 10 carbon atoms;

(ii) addition of methyl vinyl ketone to obtain 1[(5α,7α)-17-alkyl-4,5-epoxy-3-hydroxy-6-methoxy-6,14-ethenomorphinan-7-yl]ethanone or 1[(5α,7α)-17-alkyl-4,5-epoxy-3-alkoxy-6-methoxy-6,14-ethenomorphinan-7-yl]ethanone;

(iii-a) converting the acetyl group in position 7 into a tertiary alkyl alcohol having a general structure —C—(OH)—(CH₃)—R", wherein R" represents a linear, branched and/or cyclic alkyl group with 1 to 10 carbon atoms; and (iv-a) reducing the etheno group in position 18,19 to form the compound of Formula II; and (v) optionally converting the product from step (iv-a) or step (iv-b) into an addition salt, preferably a pharmaceutically acceptable salt.

In another aspect the present invention relates to a compound of Formula II,

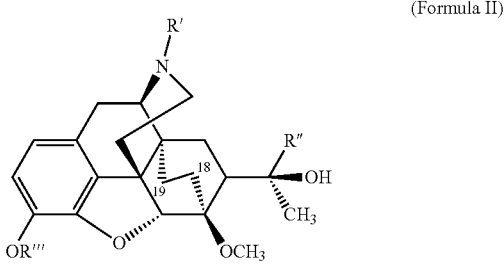

wherein in Formula II R' represents a linear, branched and/or cyclic alkyl group having 1 to 10 carbon atoms, R" represents a linear, branched and/or cyclic alkyl group having 1 to 10 carbon atoms, and R''' represents H or a linear, branched and/or cyclic alkyl group having one to 6 carbon atoms, obtained by the method according to the invention.

Also described is a pharmaceutical formulation comprising the compound of Formula II obtained by the method according the invention.

Also described is the pharmaceutical formulation comprising the compound of Formula II obtained by the method according the invention for use in a medicine.

In addition, described is the use of the compound of Formula II obtained by the method according the invention in a pharmaceutical formulation.

Further embodiments are disclosed in the dependent claims and can be taken from the following description and examples, without being limited thereto.

DETAILED DESCRIPTION OF THE PRESENT INVENTION

All ranges disclosed herein are to be considered to be supplemented by the term "about", unless clearly defined to the contrary or otherwise clear from the context.

All numbers or percentages relating to amounts of a substance within this application are given in wt. %, unless clearly defined to the contrary or otherwise clear from the context.

In regard to this invention, a reference to a linear, branched and/or cyclic alkyl group refers to linear alkyl groups, branched alkyl groups, cyclic alkyl groups, cyclic alkyl groups with linear or branched alkyl groups attached, i.e. cycloalkylalkyl groups, and linear or branched alkyl groups with a cyclic alkyl group attached, i.e. alkylcycloalkyl groups, wherein the cyclic alkyl group in the alkylcycloalkyl groups can also have linear or branched alkyl groups attached.

The present invention relates in a first aspect to a method of preparing a compound of Formula II, or a salt thereof, from a compound of Formula I, wherein in Formula II R' represents a linear, branched and/or cyclic alkyl group having 1 to 10 carbon atoms, R" represents a linear, branched and/or cyclic alkyl group having 1 to 10 carbon atoms, and R'" represents H or a linear, branched and/or cyclic alkyl group having 1 to 6 carbon atoms, comprising:

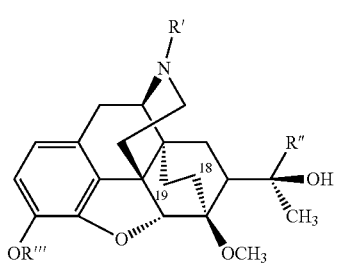

(Formula II)

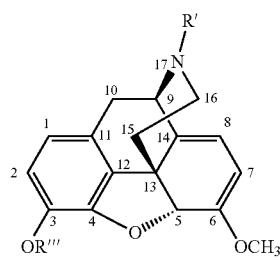

(Formula I)

le;2q(i) optionally replacing the group R in the compound of Formula I, wherein R is H or methyl, by a group R', being different from R, selected from H or a linear, branched and/or cyclic alkyl group having 1 to 10 carbon atoms;

(ii) addition of methyl vinyl ketone to obtain 1[(5α,7α)-17-alkyl-4,5-epoxy-3-hydroxy-6-methoxy-6,14-ethenomorphinan-7-yl]ethanone or 1[(5α,7α)-17-alkyl-4,5-epoxy-3-alkoxy-6-methoxy-6,14-ethenomorphinan-7-yl]ethanone;

(iii-a) converting the acetyl group in position 7 into a tertiary alkyl alcohol having a general structure —C—(OH)—(CH3)-R", wherein R" represents a linear, branched and/or cyclic alkyl group with 1 to 10 carbon atoms; and (iv-a) reducing the etheno group in position 18,19 to form the compound of Formula II; and (v) optionally converting the product from step (iv-a) or step (iv-b) into an addition salt, preferably a pharmaceutically acceptable salt.

Further described is a method of preparing a compound of Formula II, or a salt thereof, from a compound of Formula I, wherein in Formula II R' represents a linear, branched and/or cyclic alkyl group having 1 to 10 carbon atoms, R" represents a linear, branched and/or cyclic alkyl group having 1 to 10 carbon atoms, and R'" represents H or a linear, branched and/or cyclic alkyl group having 1 to 6 carbon atoms, comprising:

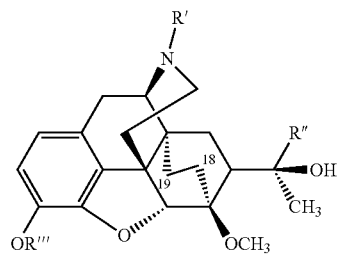

(Formula II)

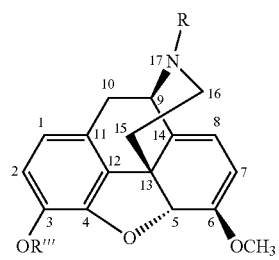

(Formula I)

(i) optionally replacing the group R in the compound of Formula I, wherein R is H or methyl, by a group R', being different from R, selected from H or a linear, branched and/or cyclic alkyl group having 1 to 10 carbon atoms;

(ii) addition of methyl vinyl ketone to obtain 1-[(5α,7α)-17-alkyl-4,5-epoxy-3-hydroxy-6-methoxy-6,14-ethenomorphinan-7-yl]ethanone or 1-[(5α,7α)-17-alkyl-4,5-epoxy-3-alkoxy-6-methoxy-6,14-ethenomorphinan-7-yl]ethanone;

(iii-b) reducing the etheno group in position 18,19; and (iv-b) converting the acetyl group in position 7 into a tertiary alkyl alcohol having a general structure —C—(OH)—(CH3)-R", wherein R" represents a linear, branched and/or cyclic alkyl group with 1 to 10 carbon atoms, to form the compound of Formula II; and (v) optionally converting the product from step (iv-a) or step (iv-b) into an addition salt, preferably a pharmaceutically acceptable salt.

In Formulas I and II, R, R', R" and R'" can be the same or different.

According to certain aspects, the present invention relates to a method of preparing a compound of Formula IV, or a salt thereof, from oripavine, wherein in Formula IV R' represents a linear, branched and/or cyclic alkyl group having 1 to 10 carbon atoms and R" represents a linear, branched and/or cyclic alkyl group having 1 to 10 carbon atoms comprising:

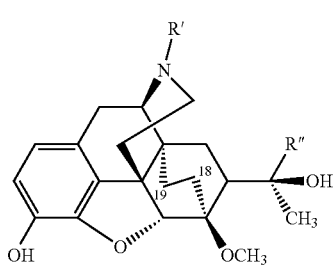

(Formula IV)

(i) optionally replacing the 17-N methyl group in oripavine by a group R being a linear, branched and/or cyclic alkyl group having 2 to 10 carbon atoms to obtain a compound of Formula III, 17-N-alkyl nororipavine;

(Formula III)

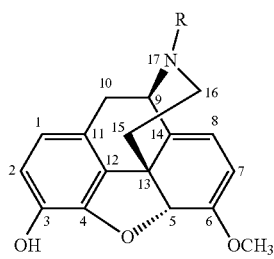

(ii) addition of methyl vinyl ketone to obtain 1-[(5α,7α)-17-alkyl-4,5-epoxy-3-hydroxy-6-methoxy-6,14-ethenomorphinan-7-yl]ethanone;

(iii-a) converting the acetyl group in position 7 into a tertiary alkyl alcohol having a general structure —C—(OH)—(CH$_3$)—R", wherein R" represents a linear, branched and/or cyclic alkyl group with 1 to 10 carbon atoms; and (iv-a) reducing the etheno group in position 18,19 to form the compound of Formula IV; or (iii-b) reducing the etheno group in position 18,19; and (iv-b) converting the acetyl group in position 7 into a tertiary alkyl alcohol having a general structure —C—(OH)—(CH$_3$)—R", wherein R" represents a linear, branched and/or cyclic alkyl group with 1 to 10 carbon atoms, to form the compound of Formula IV; and (v) optionally converting the product from step (iv-a) or step (iv-b) into an addition salt, preferably a pharmaceutically acceptable salt.

According to certain aspects, the present invention relates to a method of preparing a compound of Formula IV, or a salt thereof, from oripavine, wherein in Formula IV R' represents a linear, branched and/or cyclic alkyl group having 1 to 10 carbon atoms and R" represents a linear, branched and/or cyclic alkyl group having 1 to 10 carbon atoms comprising:

(Formula IV)

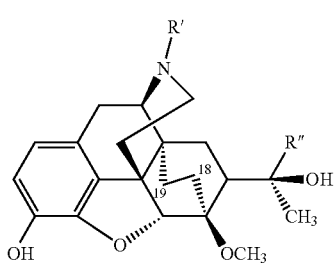

(i) optionally replacing the 17-N methyl group in oripavine by a group R being a linear, branched and/or cyclic alkyl group having 2 to 10 carbon atoms to obtain a compound of Formula III, 17-N-alkyl nororipavine;

(Formula III)

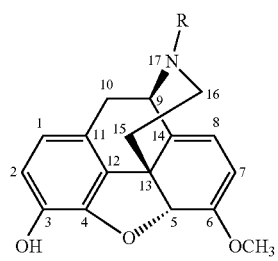

(ii) addition of methyl vinyl ketone to obtain 1[(5α,7α)-17-alkyl-4,5-epoxy-3-hydroxy-6-methoxy-6,14-ethenomorphinan-7-yl]ethanone;

(iii-a) converting the acetyl group in position 7 into a tertiary alkyl alcohol having a general structure —C—(OH)—(CH$_3$)—R", wherein R" represents a linear, branched and/or cyclic alkyl group with 1 to 10 carbon atoms; and (iv-a) reducing the etheno group in position 18,19 to form the compound of Formula IV; and (v) optionally converting the product from step (iv-a) or step (iv-b) into an addition salt, preferably a pharmaceutically acceptable salt.

In addition, described is a method of preparing a compound of Formula IV, or a salt thereof, from oripavine, wherein in Formula IV R' represents a linear, branched and/or cyclic alkyl group having 1 to 10 carbon atoms and R" represents a linear, branched and/or cyclic alkyl group having 1 to 10 carbon atoms comprising:

(Formula IV)

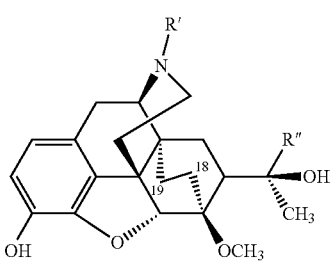

(i) optionally replacing the 17-N methyl group in oripavine by a group R being a linear, branched and/or cyclic alkyl group having 2 to 10 carbon atoms to obtain a compound of Formula III, 17-N-alkyl nororipavine;

(Formula III)

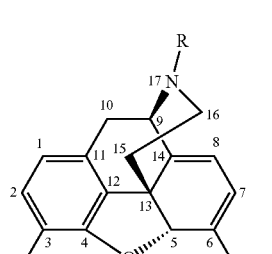

(ii) addition of methyl vinyl ketone to obtain 1[(5α,7α)-17-alkyl-4,5-epoxy-3-hydroxy-6-methoxy-6,14-ethenomorphinan-7-yl]ethanone;
(iii-b) reducing the etheno group in position 18,19; and
(iv-b) converting the acetyl group in position 7 into a tertiary alkyl alcohol having a general structure —C—(OH)—(CH$_3$)—R'", wherein R'" represents a linear, branched and/or cyclic alkyl group with 1 to 10 carbon atoms, to form the compound of Formula IV; and
(v) optionally converting the product from step (iv-a) or step (iv-b) into an addition salt, preferably a pharmaceutically acceptable salt.

In Formulas III and IV, R, R', and R" can be the same or different.

It is understood that all these reaction steps (i) to (v) work under different conditions. In general, there are no limitations in the choice of the solvents, temperature, reaction time, or gas pressure.

The optional step (i) is a nucleophilic substitution, not particularly limited, and can be suitably carried out as known from general synthesis methods. Step (i) consists of two sub-steps to replace a 17-N—R group by a different 17-N-alkyl group. First the alkyl group R' is introduced and R is released. For example, the compound of Formula I, e.g. oripavine or thebaine, can react with an alkyl R'—X' wherein R' represents a linear, branched and/or cyclic alkyl group having 1 to 10 carbon atoms and X' represents a suitable leaving group like halogenide, leading to an addition of alkyl and subsequently the 17-N-methyl group or the H in position 17 can be removed to obtain 17-N-alkyl nororipavine in case R'" is H. Depending on starting and target molecule, step (i) needs to be carried out or not. Preferably R is a methyl group and R' can be a linear, branched and/or cyclic alkyl group having 1 to 10 carbon atoms.

In certain embodiments, the reaction of step (i) can be carried out at a temperature between 0 and 100° C., e.g. 50 to 90° C., preferably 70 to 85° C., for a total time of less than 24 hours, wherein e.g. the addition step of an alkyl group can be carried out in less than 20 hours and the elimination of the methyl group or H in less than 4 hours. A solvent can be suitably selected for the reaction and is not particularly limited in step (i). It can be e.g. DMF (dimethylformamide) in the addition of an alkyl group and DMSO (dimethylsulfoxide) in the elimination step from the quaternary amine.

Oripavine or thebaine, serving as possible and preferred starting materials, can thereby be obtained from known sources. Preferably oripavine and thebaine are extracted from the latex of certain types of papaveraceae. It is also possible to use synthetic or semi-synthetic oripavine or thebaine in the present method.

In certain embodiments a different starting material than oripavine can be used and thus the substitution of the original alkyl group to the tertiary amine in step (i) by a different one is not limited to the substitution of methyl by methyl cyclopropyl. In contrary, all kinds of linear, or branched alkyl groups having a total of 3 to 10 carbon atoms as well as alkyl groups having a ring structure can be used. In case the alkyl group contains a ring the ring may have 3 to 7 carbon atoms. Preferably oripavine or thebaine is used as educt and converted to buprenorphine or 18,19-dihydroetorphine. Further preferably oripavine or thebaine is converted to buprenorphine, and according to certain aspects oripavine is converted to buprenorphine.

In preferred embodiments, the group R' is a linear, branched and/or cyclic alkyl group having 1 to 10 carbon atoms, e.g. a methyl group. In embodiments wherein R' contains a cyclic group, e.g. an alkyl cycloalkyl group, R' has preferably 3 to 10 carbon atoms, further preferably 3 to 7 carbon atoms, more preferably 3 to 5 carbon atoms. A suitable and preferred example is e.g. a methylcyclopropyl group.

The addition of methylvinylketone in step (ii) can be suitably carried out using e.g. a Diels-Alder-reaction. The addition in step (ii) can be an addition of methyl vinyl ketone (MVK) by a Diels-Alder reaction to introduce an etheno group between the atoms in position 6 and 14. While adding the etheno group between the atoms in position 6 and 14, an acetyl group is attached in position 7 in such a reaction.

In certain embodiments, the reaction can be carried out at a temperature between 0 and 100° C., e.g. 50 to 90° C., for a total time of less than 24 hours, e.g. less than 15 hours. A solvent for the reaction can be suitably selected and is not particularly limited in step (ii).

The educt in step (ii) can be either the compound of Formula I, e.g. oripavine or thebaine, if the optional step (i) is not carried out, or can be e.g. the 17-N-alkylated product of the compound of formula (I) if step (i) is carried out.

Step (iii-a), respectively step (iv-b) represent the conversion of the acetyl group in position 7 of the ring structure by a suitable reaction, e.g. by a Grignard reaction with R"MgX, wherein R" represents a linear, branched and/or cyclic alkyl group with 1 to 10 carbon atoms, and X represents a halogen to form the alcohol. Step (iii-a), respectively step (iv-b) can also be seen as a conversion of the acetyl group in position 7 into a 18,19-dehydrobuprenorphine derivative/analogue having different groups R' and/or R" and/or R'", wherein R', R" and R'" can be the same or different, e.g. by reaction with R"MgX, wherein R" represents a linear, branched and/or cyclic alkyl group with 1 to 10 carbon atoms, and X represents a halogen.

In certain embodiments, the Grignard reaction in step (iii-a), respectively step (iv-b) can be conducted with any suitable substance to convert the acetyl group in position 7 to an alcohol. For example tertiary butyl magnesium chloride can be used to form a desired di-methyl butanol group (e-g—a 3-(2,2-dimethylbutan-3-ol group), or n-propyl magnesium chloride is used to form the desired 2-pentanol group. It is understood that all kinds of linear, branched and/or alkyl groups having a total of 1 to 10 carbon atoms, preferably 3 to 10 carbon atoms, further preferably 3 to 7 carbon atoms as well as alkyl groups having a ring structure can be used. In case the alkyl group contains a ring the ring may have e.g. 3 to 7 carbon atoms. For example, R" can be a tert-butyl group or an n-propyl group, wherein R'" can be e.g. H or CH$_3$, e.g. H.

In certain embodiments, the reaction can be carried out at a temperature between 0 and 100° C., e.g. 50 to 90° C., preferably 55 to 80° C., for a total time of less than 24 hours, e.g. less than 15 hours. A solvent for the reaction in step (iii-a), respectively step (iv-b), can be suitably selected and is not particularly limited. According to preferred embodiments, the solvent in step (iii-a) or (iv-b) comprises an ether or is an ether.

Further preferably the solvent in step (iii-a) or (iv-b) comprises an ether like tert-butylmethylether, 2-methyl-tetrahydrofuran, diethylether, dimethoxyethane, dimethoxymethane or mixtures thereof, particularly tert-butylmethylether, 2-methyl-tetrahydrofuran, dimethoxymethane or mixtures thereof. The solvent used in (iii-a) or (iv-b) can further comprise solvents like dioxane, tetrahydrofuran or cylcopentyl-methyl-ether, which are less preferable as sole solvents, though.

In certain aspects, the solvent in step (iii-a) or (iv-b) comprises an ether like tert-butylmethylether, 2-methyl-tetrahydrofuran, diethylether, dimethoxyethane, dimethoxymethane or mixtures thereof with a least 30 wt. %, preferably at least 40 wt. %, with regard to all solvents used in step (iii-a) or (iv-b), particularly tert-butylmethylether, 2-methyl-tetrahydrofuran, dimethoxymethane or mixtures thereof. In this regard, other solvents like dioxane, tetrahydrofuran or cylcopentyl-methyl-ether can be contained in the solvent mixture.

Preferably, step (iii-a) or (iv-b) is carried out using essentially tert-butylmethylether, 2-methyl-tetrahydrofuran, diethylether, dimethoxyethane, dimethoxymethane or mixtures thereof, particularly tert-butylmethylether, 2-methyl-tetrahydrofuran, dimethoxymethane or mixtures thereof, as solvent. In this regard, other solvents like dioxane, tetrahydrofuran or cylcopentyl-methyl-ether can be contained in the solvent mixture with less than 10 wt. %, based on the total weight of all solvents used in step (iii-a) or (iv-b).

According to certain embodiments, a linear, branched and/or a ring containing reagent R"MgX is used in step (iii-a) or (iv-b) for the conversion of the acetyl group into the hydroxyalkyl group, wherein R" represents a linear, branched and/or cyclic alkyl group with 1 to 10 carbon atoms, and X represents a halogen.

Step (iv-a), respectively step (iii-b) represents a reduction of the 18,19 etheno group bond to form the desired substance as free base, e.g. a reduction of the etheno group in position 18,19 to get buprenorphine or the desired analogue thereof. In certain embodiments the hydrogenation of the carbon-carbon double bound as disclosed to be step (iv) can be executed with any known technology. In certain embodiments conventional hydrogenation is indicated, in certain other embodiments the use of a hydrogen transfer agent is indicated. In the second case both an external and an internal hydrogen source can be used. Preferably this step is carried out with hydrogen gas and any appropriate catalyst. A preferred reaction system is hydrogen gas and a palladium on carbon as catalyst.

The reaction can be carried out using e.g. a hydrogenation reaction with a suitable catalyst like palladium on carbon, e.g. Pd/C with 5% Pd, or any other suitable catalyst. The pressure for the hydrogen in the hydrogenation reaction can be suitably selected and can be e.g. between 4 and 20 bar. Also different pressures can be used in step (iv-a) and step (iii-b). For example, a suitable pressure in step (iii-b) can be between 4-10 bar, whereas a suitable pressure in step (iv-a) can be between 11 and 20 bar. Further, a solvent in step (iv-a), respectively step (iii-b), can be suitably selected and can be e.g. an alcohol like methanol, ethanol, propanol like n-propanol or i-propanol, or butanol, etc. In addition, the reaction time in step (iv-a) or step (iii-b) is not particularly limited, and also not the reaction time. Au suitable reaction temperature can be e.g. between 10 and 100° C., preferably between 40 and 80° C.

In this regard it has been found that steps (iii-b) and (iv-b) can be swapped while maintaining all advantages of the method. It has further been found that step (iv-b) can be conducted prior step (iii-b) without losing performance, yield or other advantages of the actual invention, resulting in a reaction with steps (iii-a) and (iv-a). When carrying out steps (iii-a) and (iv-a), the reaction with the generally lower reaction yield is carried out first, e.g. in case of a Grignard reaction being between 50 and 65%, with a conversion between 75 and 85%. In contrast, the hydration step (iv-a) generally has 100% conversion with yields between 75 to 90%, as can be seen e.g. in the Examples. This way solvent amount and energy consumption in the overall process can be reduced, as will be shown for the Examples below.

The substance obtained after step (iv-a) or step (iv-b) that way can be transferred into an addition salt, preferably into a pharmaceutically acceptable acid addition salts, using standard procedures as dissolving the substance in an appropriate solvent, adding the acid and crystallizing.

In certain embodiments, the optional step (v) can be suitably carried out with e.g. the compound of Formula (II) and a suitable, preferably pharmaceutical acceptable, inorganic acid like HCl, HBr, H3PO4, H2SO4, HNO3, or a suitable, preferably pharmaceutical acceptable, organic acid like maleic acid, malic acid, malonic acid, methanesulfonic acid, or 4-toluenesulfonyl acid. The solvent and reaction conditions like temperature and pressure are not particularly limited and can be suitably determined based on the compound of Formula (II) to be reacted and the acid. In certain embodiments, buprenorphine can be reacted with an acid to produce a buprenorphine salt, for example buprenorphine hydrochloride. The production of a buprenorphine salt, e.g. buprenorphine HCl, can be accomplished, and is not limited to, by any known reaction routes after buprenorphine base has been formed.

According to certain embodiments, R'" represents a linear, branched and/or cyclic alkyl group having 1 to 6 carbon atoms in the compound of Formula I, e.g. thebaine. In such embodiments R'" can be converted to H at any suitable time during the present method, i.e. before step (i), after step (i), after step (ii), after step (iii-a) or (iii-b) or step (iv-a) or (iv-b) or after step (v). In certain embodiments, R'" is converted to H before step (i) or after step (i) or after step (ii), preferably before step (i). The conversion of the alkoxy group in position 3 into a hydroxy group in position 3 is known in the art and can be suitably carried out using known methods (see e.g. Andre, J-D et al., "*O-Demethylation of Opioid Derivatives with Methane Sulfonic Acid/Methionine: Application to the Synthesis of Naloxone and Analogues*", Synthetic Comm., 22(16), 2313-2327 (1992).

According to certain embodiments R'" is H. In this case normally R'" is not converted anymore.

According to certain embodiments, R' represents methyl-cyclopropyl and R" represents tert-butyl or R' represents methyl and R" represents n-propyl in formula II, with R'" being H in both cases.

Further disclosed is a product obtained by the present method.

According to another aspect, the present invention relates to a compound of Formula II,

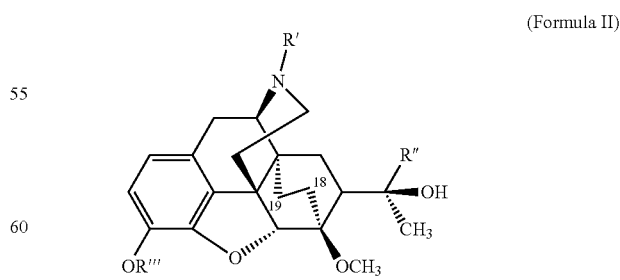

(Formula II)

wherein in Formula II R' represents a linear, branched and/or cyclic alkyl group having 1 to 10 carbon atoms, R" represents a linear, branched and/or cyclic alkyl group having 1 to 10 carbon atoms, and R'" represents H or a linear, branched and/or cyclic alkyl group having 1 to 6 carbon atoms, obtained by the method of the present invention.

According to certain embodiments the present invention relates to a compound of Formula IV,

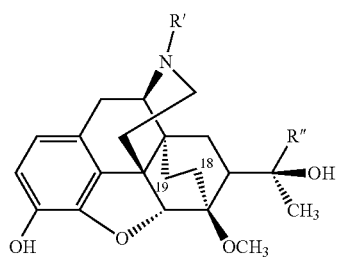

(Formula IV)

wherein in Formula IV R' represents a linear, branched and/or cyclic alkyl group having 1 to 10 carbon atoms and R" represents a linear, branched and/or cyclic alkyl group having 1 to 10 carbon atoms, which is obtained by the method of the present invention.

In addition, a pharmaceutical formulation comprising the compound of the present invention is described. Apart from that, the pharmaceutical formulation is not limited. The pharmaceutical formulation can be e.g. in the form of an injection solution, a transdermal patch or for sublingual application.

The pharmaceutical formulations can further comprise one or more pharmaceutically acceptable excipients, e.g. water, stabilizers or antifungal.

These excipients are well-known to the skilled person, e.g. from Remington, The Science and Practice of Pharmacy, $22^{nd}$ Edition, 2012, which is incorporated herein by reference in regard to pharmaceutical excipients, particularly volume 1: "The Science of Pharmacy", pages 1049-1070 or from Rowe, R. C., Sheskey, P. J., Quinn, M. E., Cook, W. G., Fenton, M. E., "Handbook of Pharmaceutical Excipients", $7^{th}$ Edition, 2012, which is incorporated herein by reference in regard to pharmaceutical excipients.

The pharmaceutical formulation can be used in medicine. Also described is the use of the compound described above in a pharmaceutical formulation.

With regard to this invention, an analogue of buprenorphine is a compound with the same ring structure as shown in formula II. Such analogues of buprenorphine or of another compound can be obtained by choosing the appropriate substituents R' and/or R" and/or R'".

In an exemplary reaction, the following steps can be included: (i) optionally the addition of alkyl to the tertiary amine of the compound of Formula I, e.g. oripavine or thebaine, to form a tertiary or quaternary amine, and removing the 17-N-methyl group or hydrogen at the 17-N to get 17-N-alkyl nororipavine or an analogue thereof with different R'", (ii) addition of methyl vinyl ketone by a Diels-Alder reaction to introduce the etheno group between the positions 6 and 14, (iii) conversion of the acetyl group by a Grignard reaction to form an alcohol, and (iv) reduction of the 18,19 etheno group to get buprenorphine or analogues thereof. It has also been found that step (iv) can be conducted prior step (iii). The product can then easily be transformed into an addition salt.

A general reaction scheme for the production of buprenorphine is shown below, which shows how exemplified buprenorphine is formed from oripavine. A whole exemplary route of synthesis according to the present invention is disclosed starting from oripavine to buprenorphine. This sequence of reactions is shorter and more efficient as conventional synthesis:

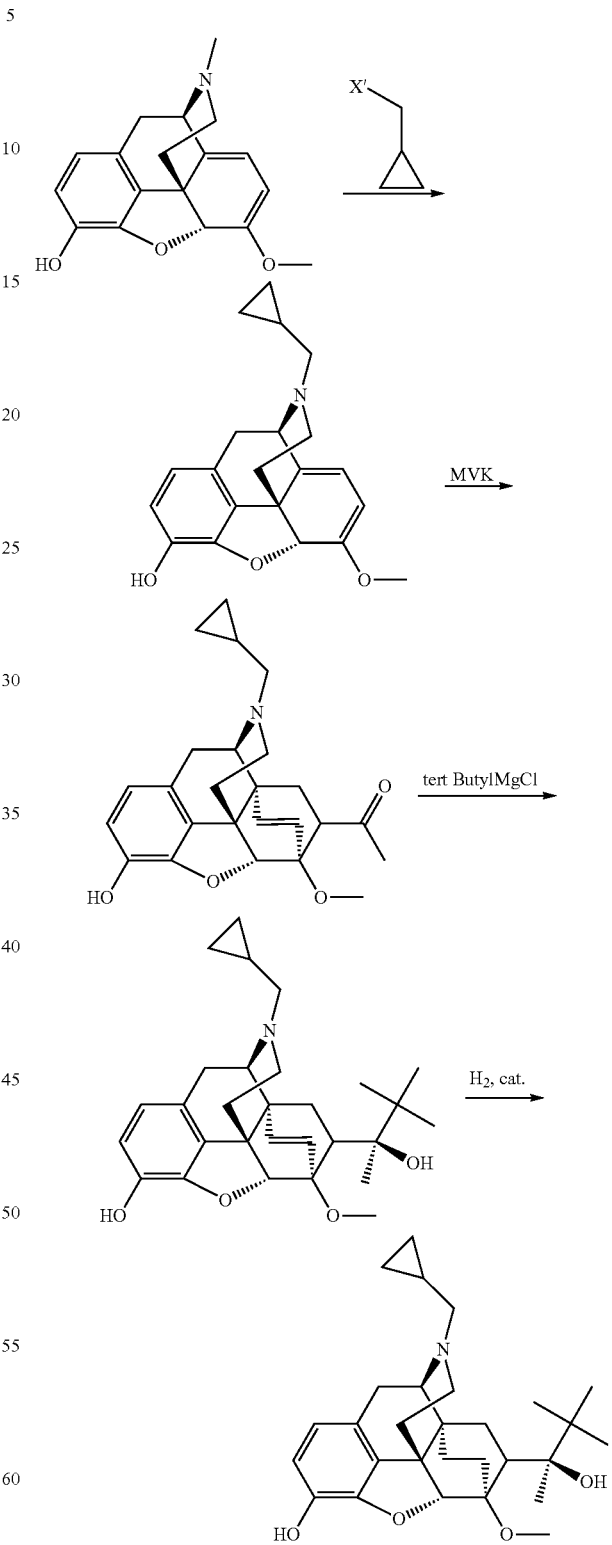

The following reaction scheme shows exemplified both possible routes of synthesis for 18,19 dihydroetorphine from oripavine.

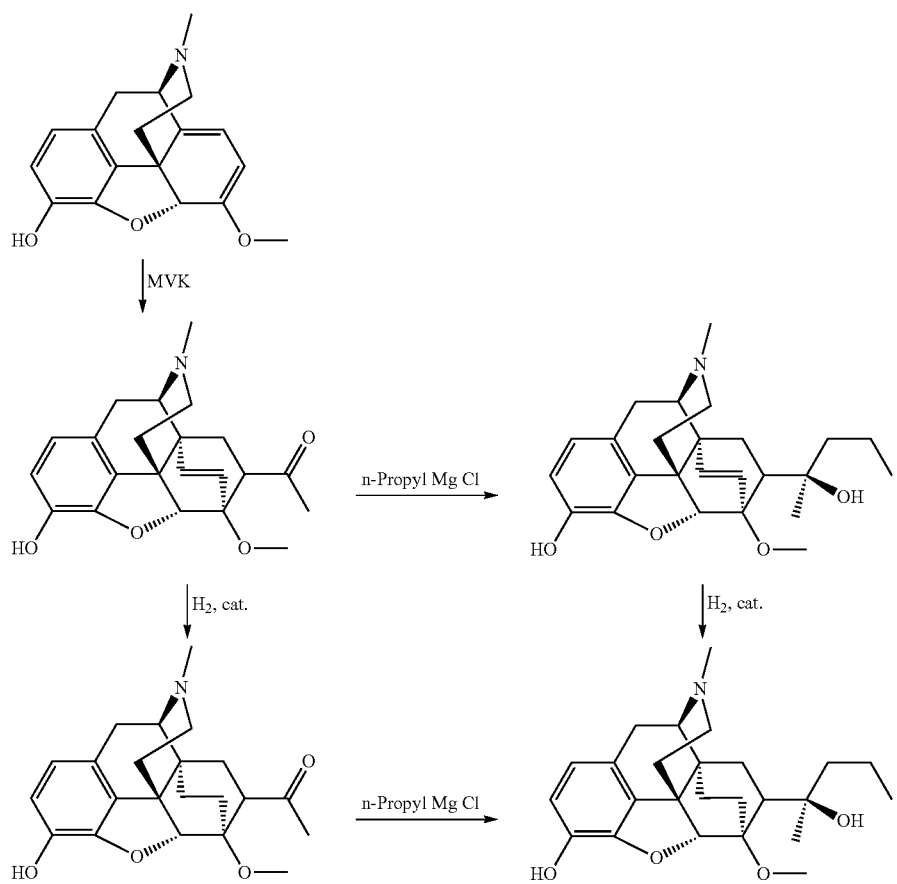

EXAMPLES

The present invention will now be described in detail with reference to several examples thereof.

However, these examples are illustrative and do not limit the scope of the invention.

Buprenorphine from Oripavine

An exemplary stepwise reaction scheme for producing buprenorphine from oripavine in 4 steps is given in the following Examples 1 to 4.

Example 1

N-cyclopropyl methyl nororipavine was synthesized using procedures as known from literature. For example the route proposed by Werner et al. (Werner, L.; Machara, A.; Adams, D. R.; Cox, D. P.; Hudlicky, T.; J. Org. Chem. 2011, 76, 4628-4634) is convenient and has a yield between 27% (chloride as halogenide) up to 55% (bromide as halogenide).

Example 2

1-[(5α,7α)-17-(cyclopropyl methyl)-4,5-epoxy-3-hydroxy-6-methoxy-6,14-ethenomorphinan-7-yl]-ethanone N-cyclopropyl methyl nororipavine from example 1 (10.0 g, 29.64 mmol) was dissolved in ethanol (60 mL). Hydroquinone (65 mg, 0.593 mmol) and methyl vinyl ketone (5.19 mL, 63.72 mmol) were added. The reaction mixture was stirred at 88° C. for 16 hrs. Thereafter, thin layer chromatography indicated no starting material. The mixture was partially distilled to give 15.0 g of distillate. The solution was cooled slowly to 0° C. during 12 hrs. and filtrated to give the desired product (8.45 g, 70%). The analyses were in agreement with literature data.

Example 3

18,19-dehydrobuprenorphine

A solution of tertiary butyl magnesium chloride (2 molar) in diethyl ether (3.1 mL) was added to tertiary butyl methyl ether (MTBE) (3.5 g). The solution was distilled to give 1.5 g of distillate. Tert-butyl methyl ether (3.5 g) was added, and the resulting mixture was distilled to give 1.5 g of distillate. This step was repeated with 2 g of tert-butyl methyl ether to give 2 g of distillate. 1[(5α, 7α)-17-(cyclopropylmethyl)-4,5-epoxy-3-hydroxy-6-methoxy-6,14-ethenomorphinan-7-yl]ethanone (0.5 g, 1.223 mmol) from example 2, dissolved in dioxane (2.5 g), was added slowly during 15 minutes at 20° C. to 22° C. The resulting white mixture was stirred during 4 h at 60° C. and then cooled to 0° C. The reaction was quenched with a saturated NH$_4$Cl solution (10 mL). After separation, the aqueous layer was extracted twice with ethyl acetate (AcOEt, 2 times 10.0 mL). The combined organic layers were dried over MgSO$_4$ and concentrated. The crude product was purified by flash chromatography (ethyl acetate/heptane: 3/2) to give 18,19-dehydrobuprenorphine (conversion: 72%, yield: 54%, 0.199 g).

TABLE 1

Conversions and yields in Example 3 using different solvents

| Example | Solvent | Conversion/% | Yield/% |
|---|---|---|---|
| 3 | MTBE | 72 | 54 |
| 3a | 2-methyl-tetrahydrofuran | 75 | 52 |
| 3b | diethylether | 68 | 48 |
| 3c | dimethoxyethane | 66 | 46 |
| 3d | dimethoxymethane | 73 | 52 |
| 3y | dioxane | <20 | <15 |
| 3z | cyclopentyl-methyl-ether | <20 | <15 |

Example 4

Buprenorphine 18,19-dehydrobuprenorphine from example 3 (2.0 g, 4.296 mmol) was dissolved in methanol (100.0 g). Palladium catalyst on carbon (0.5% Pd, 0.4 g) was added. The black mixture was stirred at 65° C. under 15 bar of hydrogen. After 60 hrs. of heating the reaction solution was cooled to 22° C. The mixture was filtered, washed with methanol (100.0 g) and concentrated. The crude buprenorphine was purified by flash chromatography (ethyl acetate/heptane: 1/1) to give 1.475 g buprenorphine (80%). 1H-NMR and 13C-NMR analyses were in agreement with literature data.

The reaction scheme for the reactions of examples 1 to 4 can be shown as follows:

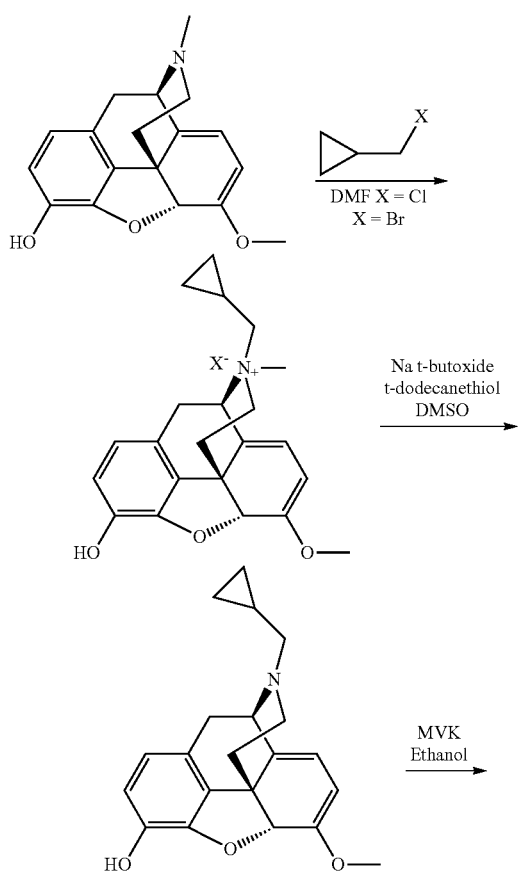

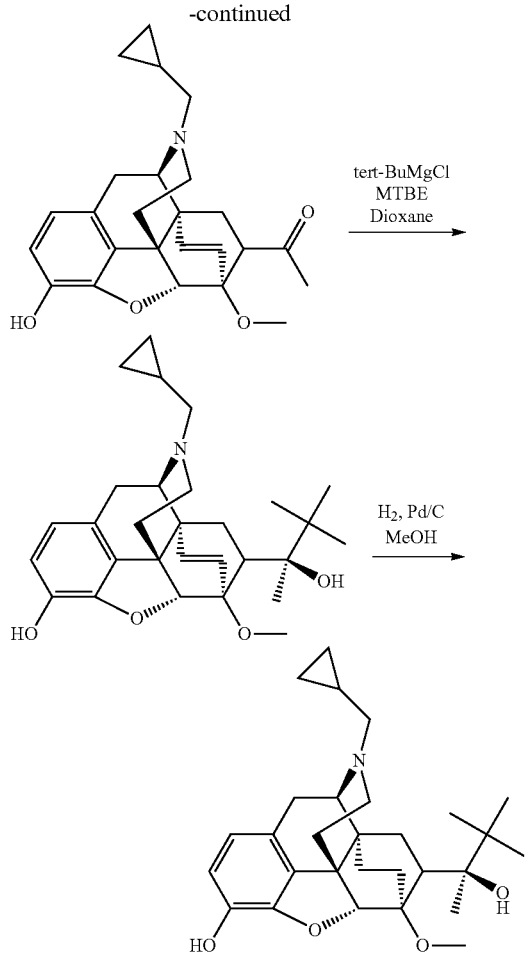

The disclosed route of synthesis gives a total yield of 16.2% for buprenorphine. This figure is an increase of about 40% compared to similar routes of synthesis.

18,19-dihydroetorphine from Oripavine

Exemplary reaction schemes for producing 18,19-dihydroetorphine from oripavine are given in the following Examples 5 to 9.

Example 5

1[(5α,7α)-17-lmethyl-4,5-epoxy-3-hydroxy-6-methoxy-6,14-ethenomorphinan-7-yl]ethanone Oripavine (200 g, 0.672 mol) was suspended in ethanol (1260 mL) with hydroquinone (1.5 g, 0.0134 mol) and methyl vinyl ketone (117.3 mL, 1.439 mol) was added. The reaction mixture was stirred at 88° C. for 22 h. The resulting solution was concentrated partially (350 g of solvent was evaporated). The mixture was cooled to 0° C. overnight. After filtration, the product was dried. Yield: 85%. The analyses were in agreement with the literature.

Example 6

Etorphine

A solution of n-propyl magnesium chloride in diethyl ether (2 molar, 6.5 mL) was added to tertiary butyl methyl ether (7.0 g). The solution was distilled to give 3.0 g of distillate. Tertiary butyl methyl ether (7.0 g) was added, the resulting mixture was distilled to give 3.0 g of distillate. This step was repeated with 5 g of tert-butyl methyl ether to give 5 g of distillate. 1-[(5α, 7α)-17-methyl-4,5-epoxy-3-hydroxy-6-methoxy-6,14-ethenomorphinan-7-yl]ethanone (0.964 g, 2.61 mmol) dissolved in dioxane (5.0 g) was added slowly during 15 min at 22° C. The resulting white mixture was stirred during 4 hrs. at 60° C. and then cooled to 0° C. The reaction was quenched with a saturated NH4Cl solution (10.0 mL). After separation, the aqueous layer was extracted twice with ethyl acetate (2 times 10 mL). The combined organic layers were dried over MgSO4 and concentrated. The crude product was purified by flash chromatography (ethyl acetate/heptane: 9/1) to give etorphine (conversion: 83%, yield: 61%, 540 mg). 1H-NMR and 13C-NMR confirmed that the desired substance was formed.

Example 7

18,19-dihydroetorphine from Etorphine

Etorphine from example 6 (0.452 g, 1.0098 mmol) was dissolved in methanol (100.0 g). Palladium catalyst on carbon (5% Pd, 0.1 g) was added. The black mixture was stirred at 65° C. under 15 bar of hydrogen. After 24 hrs. of heating, the reaction mixture was cooled to 22° C. The mixture was filtered, washed with methanol (100 g) and concentrated. The crude product was purified by flash chromatography (ethyl acetate/heptane: 3/2) to give 18,19-dihydroetorphine (yield: 77%, 0.35 g). 1H-NMR and 13C-NMR confirmed the desired substance was formed.

Example 8 (Comparative)

1-[(5α,7α)-17-methyl-4,5-epoxy-3-hydroxy-6-methoxy-6,14-ethanomorphinan-7-yl]ethanone 1[(5α,7α)-17-lmethyl-4,5-epoxy-3-hydroxy-6-methoxy-6,14-ethenomorphinan-7-yl]ethanone (5.0 g, 13.61 mmol) was dissolved in propanol (100 g). Palladium catalyst on carbon 5% Pd, 0.5 g) was added. The black mixture was stirred at 65° C. under 6 bar of hydrogen. After 16 hrs. of heating, the reaction mixture was cooled to 22° C. The mixture was filtered, washed with methanol (100 g) and concentrated to give 3.82 g (yield: 76%) 1[(5α,7α)-17-methyl-4,5-epoxy-3-hydroxy-6-methoxy-6,14-ethanomorphinan-7-yl]ethanone.

Example 9 (Comparative)

18,19-dihydroetorphine from 1-[(5α,7α)-17-methyl-4,5-epoxy-3-hydroxy-6-methoxy-6,14-ethanomorphinan-7-yl]ethanone A solution of n-propyl magnesium chloride in diethyl ether (2 molar, 25.0 mL) was added to tertiary butyl methyl ether (28.0 g). The solution was distilled to give 12.0 g of distillate. Tertiary butyl methyl ether (28.0 g) was added, the resulting mixture was distilled to give 12.0 g of distillate. This step was repeated with 17 g of tert-butyl methyl ether to give 18 g of distillate. 1-[(5α,7α)-17-(cyclopropylmethyl)-4,5-epoxy-3-hydroxy-6-methoxy-6,14-ethanomorphinan-7-yl]-ethanone (3.67 g, 9.834 mmol) dissolved in dioxane (15.0 g) were added slowly during 15 min at 22° C. The resulting mixture was stirred during 16 hrs. at 60° C. and then cooled to 0° C. The reaction was quenched with saturated NH4Cl solution (20.0 mL). After separation, the aqueous layer was extracted twice with ethyl acetate (2 times 20.0 mL). The combined organic layers were dried over MgSO4 and concentrated. The crude product was purified by flash chromatography (ethyl acetate/heptane: 1/1) to give 18,19-dihydroetorphine (yield: 61%, 2.50 g). 1H-NMR and 13C-NMR confirmed that the desired substance was formed.

The reaction schemes for the reactions of examples 5 to 9 can be shown as follows:

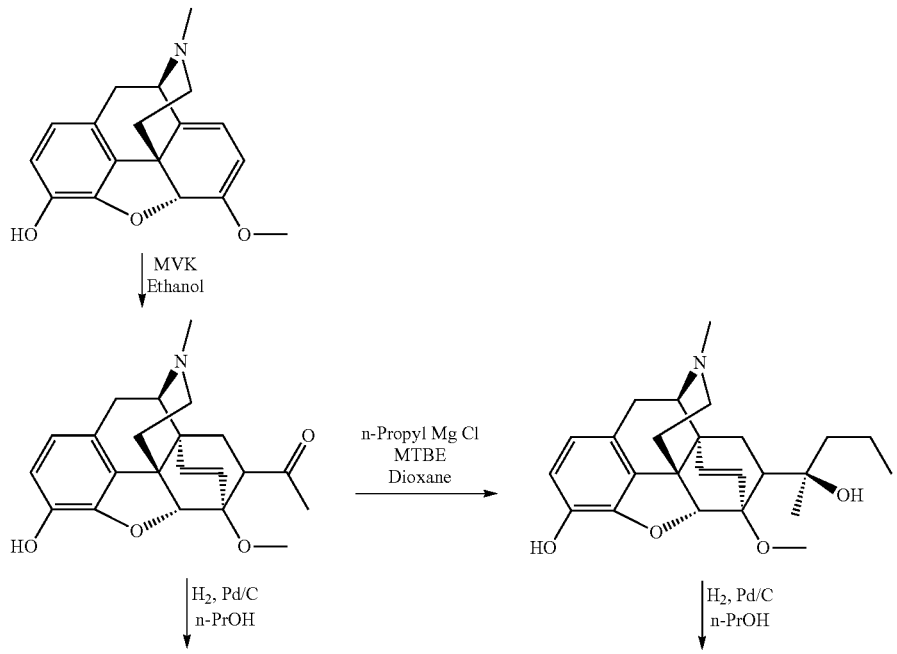

-continued

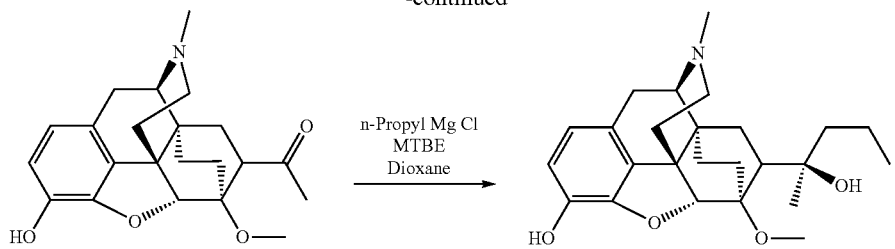

From the above Examples, it can be seen that the methods using steps (iii-a) and (iv-a) is the method wherein the step with the lower yield is carried out first. This leads to savings in solvent amounts and can also lead to reduced cost, as is shown in the following wherein it is assumed that the cost for materials and each process step are more or less the same. For example, assuming material and process cost of Euro 100,—for each reaction step in producing Buprenorphine hydrochloride, as given in the examples, the following can be calculated for exemplary conversions given for each step, wherein the conversions are identical for steps (iii-a) and (iv-b) as well as (iv-a) and (iii-b):
Reaction Sequence 1:
  Step (ii) (e.g. formation of Diels Alder adduct)→step (iii-a) (e.g. formation of Grignard adduct (70%))→step (iv-a) (e.g. formation of hydrated product (86%))→step (v) (e.g. formation of Buprenorphine HCl (90%)): Total yield: 54%
Reaction Sequence 2:
  Step (ii) (e.g. formation of Diels Alder adduct)→step (iii-b) (e.g. formation of hydrated product (86%))→step (iv-b) (e.g. formation of Grignard adduct (70%))→step (v) (e.g. formation of Buprenorphine HCl (90%)): Total yield: 54%

The first and last steps are identical, respectively. The cost for the 2 intermediate steps are thus:

0.70×100.-+0.86×0.70×100.-=130.20    Reaction sequence 1:

0.86×100.-+0.70×0.86×100.-=146.20    Reaction sequence 2:

This amounts to 12% additional costs.
Including the first and last step, the cost for 0.54 mol Buprenorphine HCl are thus 1×100.-+0.70×100.-+0.86×0.70×100.-+0.90×0.86×
   0.70×100.-=230.-                  Reaction sequence 1:

1×100.-+0.86×100.-+0.70×0.86×100.-+0.90×0.70×
   0.86×100.-=246.-                  Reaction sequence 2:

This amounts to about 6% additional costs.
Thus, reaction sequence 1 is about 6% to 12% cheaper, depending if all steps are considered or only the relevant steps.

A method has been shown herein for preparing buprenorphine, 18,19-dihydroetorphine, analogues thereof and their salts. With the present method, it is possible to obtain substances of high purity by a short synthesis even offering two different alternatives routes. Further, the need of introducing and later releasing protective groups is avoided, thus limiting efforts and costs of the present process. Also described is a method allowing performing step (iii) and step (iv) in any sequential arrangement, i.e. steps (iii-a) and (iv-a) or steps (iii-b) and (iv-b).

The current invention offers an improved method for manufacturing buprenorphine, 18,19-dihydroetorphine and other analogues thereof, as well as their acid addition salts. As starting material usually oripavine is used. With the present method, increased yields of products and intermediate products can be obtained, resulting in less side products and therefore a more economic and ecologic process. In addition, also higher isomer purity can be obtained, which can also be e.g. derived from the increased yields.

All references cited in this specification are herewith incorporated by reference in their entirety.

The present method has been described in detail with reference to certain embodiments and specified by examples. However, a skilled person will acknowledge that also other modifications, changes, or similar alterations can be made to the present invention without deviating from the spirit of the invention.

The invention claimed is:

1. A method of preparing a compound of Formula II, or a salt thereof, from a compound of Formula I, wherein in Formula II, R' represents a linear, branched and/or cyclic alkyl group having 1 to 10 carbon atoms, R" represents a linear or branched alkyl group having 1 to 10 carbon atoms, and R'" represents H or $CH_3$, comprising:

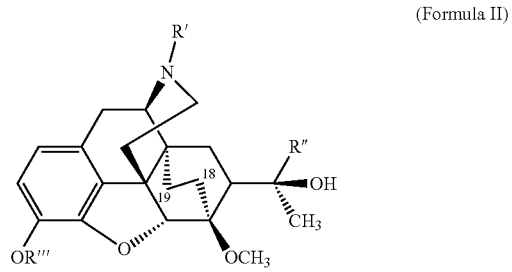

(Formula II)

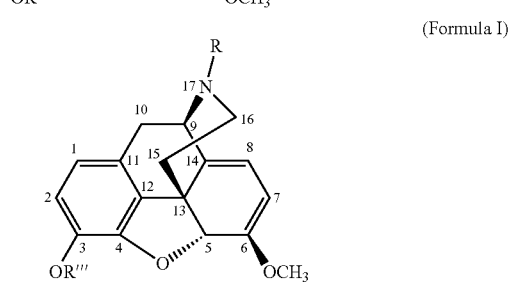

(Formula I)

(i) optionally replacing the group R in the compound of Formula I, wherein R is H or methyl, by a group R' being a linear, branched and/or cyclic alkyl group having 1 to 10 carbon atoms;
(ii) adding methyl vinyl ketone to obtain 1-[(5α,7α)-17-alkyl-4,5-epoxy-3-hydroxy-6-methoxy-6,14-ethenomorphinan-7-yl]ethanone or 1-[(5α,7α)-17-alkyl-4,5-epoxy-3-alkoxy-6-methoxy-6,14-ethenomorphinan-7-yl]ethanone;
  (iii-a) converting the acetyl group in position 7 into a tertiary alkyl alcohol having a general structure —C—(OH)—(CH3)-R″, wherein R″ represents a linear or branched alkyl group with 1 to 10 carbon atoms; and
  (iv-a) reducing the etheno group in position 18,19 to form the compound of Formula II; and
(v) optionally converting the product from step (iv-a) into an addition salt, preferably a pharmaceutically acceptable salt,
  wherein the protection of a side chain is avoided.

2. The method of claim 1, wherein step (iii-a) comprises the use of a R″MgX, wherein R″ represents a linear or branched alkyl group with 1 to 10 carbon atoms, and X represents a halogen.

3. The method of claim 1, wherein step (iii-a) comprises converting the acetyl group in position 7 into a tertiary alkyl alcohol using a solvent, wherein the solvent comprises an ether.

4. The method of claim 1, wherein step (iii-a) comprises converting the acetyl group in position 7 into a tertiary alkyl alcohol in a solvent comprising tert-butylmethylether, 2-methyl-tetrahydrofuran, diethylether, dimethoxyethane, dimethoxymethane or mixtures thereof, 2-methyl-tetrahydrofuran, dimethoxymethane or mixtures thereof.

5. The method of claim 1, wherein step (iii-a) is carried out using essentially tert-butylmethylether, 2-methyl-tetrahydrofuran, diethylether, dimethoxyethane, dimethoxymethane or mixtures thereof, particularly tert-butylmethylether, 2-methyl-tetrahydrofuran, dimethoxymethane or mixtures thereof, as solvent.

6. The method of claim 1, wherein in formula II, R′ represents methylcyclopropyl and R″ represents tert-butyl or R′ represents methyl and R″ represents n-propyl.

7. The method of claim 1, wherein in step (i) the alkyl group introduced in the 17-N position has 3 to 10 carbon atoms and has a linear, a branched and/or a ring structure.

8. The method of claim 1, wherein R′ represents $CH_3$ in the compound of Formula I.

9. The method of claim 8, wherein R‴ is converted to H before step (i) or after step (i) or after step (ii).

10. The method of claim 1, wherein R′ is H.

11. The method of claim 4, wherein the solvent comprises tert-butylmethylether.

12. A method of preparing a compound of Formula II, or a salt thereof, from a compound of Formula I, wherein in Formula II R′ represents a linear, branched and/or cyclic alkyl group having 1 to 10 carbon atoms, R″ represents a linear or branched alkyl group having 1 to 10 carbon atoms, and R‴ represents H or $CH_3$, consisting of:

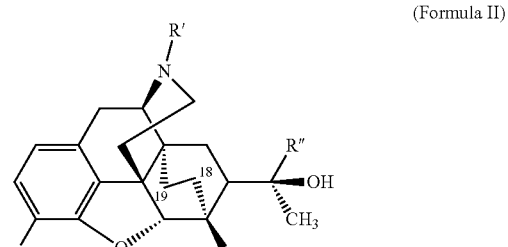

(Formula II)

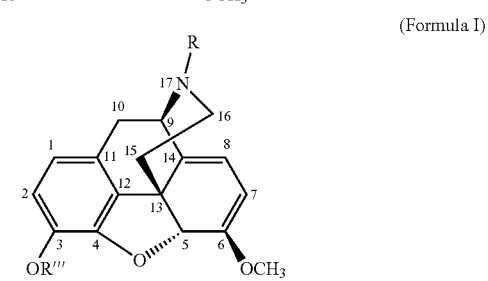

(Formula I)

(i) optionally replacing the group R in the compound of Formula I, wherein R is H or methyl, by a group R′ being a linear, branched and/or cyclic alkyl group having 1 to 10 carbon atoms;
(ii) addition of methyl vinyl ketone to obtain 1-[(5α,7α)-17-alkyl-4,5-epoxy-3-hydroxy-6-methoxy-6,14-ethenomorphinan-7-yl]ethanone or 1-[(5α,7α)-17-alkyl-4,5-epoxy-3-alkoxy-6-methoxy-6,14-ethenomorphinan-7-yl]ethanone;
  (iii-a) converting the acetyl group in position 7 into a tertiary alkyl alcohol having a general structure —C—(OH)—(CH3)-R″, wherein R″ represents a linear or branched alkyl group with 1 to 10 carbon atoms; and
  iv-a) reducing the etheno group in position 18, 19 to form the compound of Formula II; and
(v) optionally converting the product from step (iv-a) into an addition salt, preferably a pharmaceutically acceptable salt.

* * * * *